United States Patent [19]

Nakamura et al.

[11] 4,408,067
[45] Oct. 4, 1983

[54] PROCESS FOR PRODUCING CARBOXYLIC ACID ESTERS FROM NITRILES

[75] Inventors: Tomio Nakamura, Ichikawa; Shunichi Doi, Yokohama, both of Japan

[73] Assignee: Nitto Chemical Industries, Ltd., Tokyo, Japan

[21] Appl. No.: 287,655

[22] Filed: Jul. 28, 1981

Related U.S. Application Data

[63] Continuation-in-part of Ser. No. 116,198, Jan. 28, 1980, abandoned.

[30] Foreign Application Priority Data

Jan. 26, 1979 [JP] Japan .................................. 54-7218
Jan. 26, 1979 [JP] Japan .................................. 54-7219

[51] Int. Cl.³ ........................................... C07C 67/22
[52] U.S. Cl. ................................... 560/215; 560/103; 560/265; 502/241; 502/242; 502/243; 502/246; 502/258; 502/353
[58] Field of Search ............... 560/215, 212, 205, 103, 560/231, 265; 562/598

[56] References Cited

U.S. PATENT DOCUMENTS

| | | | |
|---|---|---|---|
| 2,913,486 | 11/1959 | Veatch et al. | 560/215 |
| 3,466,320 | 9/1969 | Hargis | 560/215 |
| 3,639,461 | 2/1972 | Ito et al. | 560/205 |
| 4,161,609 | 7/1979 | Cramer | 560/215 |

OTHER PUBLICATIONS

Kirk=Othmer, "Encyclopedia of Chemical Technology" 2nd Ed. (1965) vol. 8, pp. 339–340.
Finar, I. L., "Organic Chemistry" Longmans, Publ. (1963) p. 295.
Chemical Abstracts, vol. 77 (1972) #4988r.
Chemical Abstracts, vol. 87 (1977) #185,236u.

*Primary Examiner*—Natalie Trousof
*Assistant Examiner*—L. Hendriksen
*Attorney, Agent, or Firm*—Sughrue, Mion, Zinn, Macpeak and Seas

[57] ABSTRACT

In a process for preparing a carboxylic acid ester from a nitrile, water and an alcohol in the vapor phase, wherein the vapor is brought into contact with a catalyst, the improvement which comprises said catalyst being a titanium containing oxide catalyst which is obtained by hydrolyzing or neutralizing a water soluble titanium salt and subsequently calcining the resulting precipitate at a temperature in a range of about 300° to 750° C. and having the empirical formula $Ti_aMe_bX_cO_d$, wherein Me represents at least one element selected from the group consisting of Cu, Ag, Au, Mg, Zn, Sn, Pb, Zr, V, Bi, Cr, W, Mo, Mn, Fe, Co and Ni and X represents at least one element selected from the group consisting of Si and Sb and the subscripts a, b, c and d designate the atomic ratio and when a is 1, b is 0.01 to 12, c is 0 to 12 and b+c is 0.01 to 12 and d is the oxygen content of the catalyst formed by the combination of the above components.

10 Claims, No Drawings

PROCESS FOR PRODUCING CARBOXYLIC ACID ESTERS FROM NITRILES

CROSS-REFERENCE TO RELATED APPLICATIONS

This application is a continuation in part of U.S. application Ser. No. 116,198, filed on Jan. 28, 1980, now abandoned.

BACKGROUND OF THE INVENTION

1. Field of the Invention

The present invention relates to a process for producing carboxylic acid esters from nitriles. More particularly, it relates to a process for converting nitriles to carboxylic acid esters in high yields by the vapor phase catalytic reaction of the nitrile, water and alcohol in the presence of a titanium containing oxide catalyst prepared in a specific manner.

2. Description of the Prior Art

Esters, especially acrylic acid esters, methyl methacrylate, etc. are very useful materials from an industrial point of view. For example, acrylic acid esters are widely used in fibers, paints, adhesives and methacrylic acid esters are used as starting materials for synthetic resins. A liquid phase process as disclosed in Kirk-Othmer, *Encyclopedia of Chemical Technology*, 2nd Ed. (1965), Vol. 8, pages 339 to 340, and Finar, I. L., *Organic Chemistry*, Longmans, Publ. (1963), page 295 is commonly used for producing these carboxylic acid esters in which a nitrile is used as a starting material in the presence of a catalyst such as sulfuric acid or hydrochloric acid in liquid phase. When producing acrylic acid esters from acrylonitrile, acrylonitrile, alcohol and sulfuric acid are reacted in liquid phase. Such a process comprises producing acrylamide sulfate from acrylonitrile, sulfuric acid and water and subsequently adding an alcohol thereto to produce acrylic acid ester, but this process has the disadvantage that the reaction must be conducted in two stages. In addition, because the amount of sulfuric acid used must be equimolar or more than the acrylonitrile and highly concentrated sulfuric acid is applied at elevated temperatures, special consideration is needed for the selection of the materials for the reaction apparatus. Further in this process, there are problems such as a reduction in yield due to side reactions such as polymerization, production of a large amount of economically disadvantageous ammonium sulfate and the like.

A process for producing carboxylic acid esters by the vapor phase catalytic reaction of nitriles with water and alcohol in the presence of a catalyst has been proposed to eliminate the above problems. For example, U.S. Pat. No. 2,913,486 discloses a process for producing methyl acrylate, methyl methacrylate, etc. from unsaturated aliphatic nitriles using a solid esterification catalyst such as silica, silica alumina, titania, zirconia or thoria. U.S. Pat. No. 3,466,320 discloses a process for producing unsaturated aliphatic acid esters from the corresponding unsaturated nitriles using an esterification catalyst containing niobium pentoxide, and Japanese Patent Application (OPI) No. 25120/72 (The term "OPI" as used herein refers to a "published unexamined Japanese patent application".) discloses a process for producing acrylic acid esters from acrylonitrile using a catalyst containing boron trioxide. In these processes carboxylic acid esters are produced from nitriles in one stage, and although there was no need to use sulfuric acid unlike the conventional process, the percent conversion to the carboxylic acid esters from the nitriles is only about 10% and thus these processes are not satisfactory from the standpoint of the catalytic activity. This indicates that while conventional solid esterification catalysts exhibit catalytic activities that provide esters in theoretical yields in the reactions of organic acids and alcohols, they do not have sufficient catalytic activities for the reactions of nitriles and alcohols.

SUMMARY OF THE INVENTION

The present invention is therefore directed to solving the aforementioned problems and has for its object to provide a process for producing carboxylic acid esters with a high percent conversion of nitrile and an excellent selectivity for the ester when reacting the nitrile, water and alcohol to directly produce the corresponding carboxylic acid ester. This object is attained using, as a catalyst, a titanium containing oxide obtained by hydrolyzing or neutralizing a water soluble titanium salt, mixing the resulting precipitate with at least one specific element and calcining the mixture under certain temperature conditions.

Thus, the present invention provides a process for producing carboxylic acid esters and in particular alpha, beta unsaturated acid esters from nitriles characterized by vapor phase catalytic reaction of a nitrile, water and an alcohol at a temperature of about 100° to 500° C. in the presence of a titanium containing oxide catalyst, which is obtained by hydrolyzing or neutralizing a water soluble titanium salt and subsequently calcining the resulting precipitate at a temperature of about 300° to 750° C. and having the empirical formula $Ti_aMe_bX_cO_d$, wherein Me represents at least one element selected from the group consisting of Cu, Ag, Au, Mg, Zn, Sn, Pb, Zr, V, Bi, Cr, W, Mo, Mn, Fe, Co and Ni and X represents at least one element selected from the group consisting of Si and Sb and the subscripts a, b, c, and d designate the atomic ratio and when a is 1, b is 0.01 to 12, c is 0 to 12, b+c is 0.01 to 12, and d is the oxygen content of the catalyst formed by the combination of the above components.

DETAILED DESCRIPTION OF THE INVENTION

As the catalyst in the present invention, there is employed a titanium containing oxide catalyst containing titanium and at least one element (Me) selected from the group consisting of copper, silver, gold, magnesium, zinc, tin, lead, zirconium, vanadium, bismuth, chromium, molybdenum, manganese, tungsten, iron, cobalt and nickel, or a titanium containing oxide catalyst containing at least one element (X) selected from the group consisting of silicon and antimony in addition to the above-described components (Ti+Me). Preferred examples of the elements (Me) are copper, silver, gold, tin, lead, zirconium, vanadium, bismuth, molybdenum and tungsten, most preferably copper, tin, vanadium, molybdenum and tungsten. Preferred example of the elements (X) is silicon. In thus the catalysts used in the present invention, the atomic ratio of the total of the elements (Me) to titanium is about 0.01 to 12 per one atom of titanium, preferably 0.01 to 8, the atomic ratio of the total of the elements (X) to titanium is about 0 to 12 per one atom of titanium, preferably 0.01 to 12 and the atomic ratio of the total of the elements (Me+X) to titanium is about 0.01 to 12 per one atom of titanium, preferably 0.02 to 12.

The titanium containing oxide catalyst used in the present invention is produced by adding an aqueous alkali solution to an aqueous solution of a water soluble titanium compound, e.g., titanium chloride, nitrate, sulfate or their mixture to hydrolyze to neutralize the titanium salt, mixing the resulting precipitate with at least one specific element as described above and calcining the mixture at a temperature of about 300° to 750° C. As the alkali, ammonia, ammonium carbonate, sodium carbonate, sodium hydroxide, etc. may be employed. The temperature for the hydrolysis or neutralization is typically about 10° to 100° C. For instance, a catalyst containing titanium and copper may be produced by neutralizing titanium tetrachloride with ammonia water to form a precipitate, adding thereto copper hydroxide or oxide produced by adding alkali to an aqueous solution of a copper salt such as copper nitrate, copper sulfate, etc., mixing them thoroughly, molding and calcining.

A catalyst containing titanium and tungsten may be produced by neutralizing titanium sulfate with ammonia water to form a precipitate, adding thereto ammonium tungstate and mixing them thoroughly before drying and calcining to thermally decompose the tungsten component into the oxide.

It is not preferred to produce the titanium containing oxide catalyst by adding an aqueous alkali solution to an aqueous solution of a mixture of the water soluble titanium salt and the aforementioned compound(s) to hydrolyze or neutralize and calcining the resulting precipitate, because the catalytic activity of the titanium containing oxide catalyst is not adequate. On the other hand, where the element is silicon, a mixture of the silicon compounds or silica sol and the water soluble titanium salt or an aqueous solution of the mixture can be hydrolyzed or neutralized and the resulting titanium containing oxide catalyst can be calcined without a loss in catalytic activity. For instance, a catalyst containing titanium, tin and silicon may be produced by mixing titanium tetrachloride with ethyl silicate $Si(OEt)_4$, adding the mixture to water, neutralizing the aqueous solution of the mixture with ammonia water to form a precipitate, adding thereto a precipitate produced by neutralizing tin chloride with ammonia water, mixing them thoroughly, drying and calcining.

The starting materials for the specific elements constituting the catalyst may be chosen from various oxides, hydroxides, chlorides, nitrates, organic acid salts, etc. of the respective components. In addition, those compounds which can be converted into the hydroxides or oxides by chemical treatment, calcination, etc. may also be employed.

In the preparation of the catalyst in the present invention, it is necessary to calcine the mixture of the precipitate obtained by hydrolyzing or neutralizing the water soluble titanium salt and the compound of the specific element(s) at a temperature of about 300° to 750° C., preferably 350° to 650° C., whereby the catalytic activity is improved. The calcination is preferably conducted in an oxygen containing atmospere, e.g., in air, and the time for the calcination is preferably about 0.5 to 48 hours. If the calcination temperature is below 300° C., the change of the catalytic activity with time is remarkable, whereas with a temperature of 800° C. or higher, the yield of carboxylic acid ester is reduced. Thus temperatures outside the above range are undesirable.

The catalyst in the present invention may be supported on a carrier. As the carrier, for example, α-alumina, Carborundum, silica alumina or the like may be employed.

The reactants in the present invention are the nitrile, water and alcohol. The nitriles used in this invention are nitriles such as R-CN wherein R represents an alkyl group having 1 to 4 carbon atoms, an alkenyl group having 2 to 4 carbon atoms, a phenyl group or a phenyl group substituted by a methyl group or a halogen atom. Examples of the nitrile are acetonitrile, propionitrile, acrylonitrile, methacrylonitrile, benzonitrile, etc. The alcohols used in this invention are primary or secondary alcohols having 1 to 6 carbon atoms. Examples of the alcohol are methyl alcohol, ethyl alcohol, n-propyl alcohol, isopropyl alcohol, butyl alcohol, etc., depending on the carboxylic acid ester desired.

The reaction in accordance with the present invention is carried out by a vapor phase process, the mode of which may be any such as a fixed bed process, fluidized bed process, etc. The amounts of nitrile, water and alcohol supplied for the reaction can vary over a wide range, but preferably 1 to 20 moles and most preferably 1.5 to 10 moles of water, and 1 to 10 moles and most preferably 1 to 5 moles of alcohol are employed per mole of the nitrile. A reaction temperature of about 100° C. or higher is effective with temperatures of about 150° to 500° C. being preferred. If the reaction temperature is below 100° C., the reaction rate is too slow to be practical. The reaction gas is preferably contacted with the catalyst at a space velocity of about 10 to 10,000 hr$^{-1}$, and most preferably about 10 to 5,000 hr$^{-1}$. The reaction is satisfactorily conducted at atmospheric pressure, but may also be conducted at elevated or reduced pressures as desired. In addition, on carrying out the reaction, in contacting the reactants with the catalyst under the aforementioned conditions; it may be desired to conduct the reaction by diluting the gas with a gas which does not interfere with the reaction (e.g., an inert gas such as nitrogen, etc.) for better effects on inhibition of the side reactions, inhibition of polymerization of the product, improvements in percents conversion, selectivity, etc.

The present invention will be more particularly described in the following examples. It is to be understood that the present invention is not limited to these examples.

EXAMPLES

The method used for testing the prepared catalysts is as follows:

50 ml of a catalyst is filled into a column reactor having an inner diameter of 17 mm and is then heated to a specified temperature. A gas having the following composition is charged to the column at a specified space velocity. The reaction pressure is atmospheric pressure. The reaction gas is quantitatively analyzed by the gas chromatograph.

Water/Nitrile=4 (molar ratio)
Alcohol/Nitrile=3 (molar ratio)
Nitrogen/Nitrile=5 (molar ratio)

Preparation of Catalysts

In the following examples, Catalysts 1 to 22 were prepared according to the process of the present invention and Catalysts 23 to 35 were prepared for comparative purposes in order to clarify the significance of the present invention.

Each catalyst was prepared as follows and the catalyst composition is expressed as the empirical formula, supposing that the catalyst form is oxide.

Catalyst 1

(I) 50.0 g of copper sulfate $CuSO_4.5H_2O$ was dissolved in 400 ml of water and the temperature of the aqueous solution was raised to 70° C. To this solution was added a solution of 30 g of sodium hydroxide in 200 ml of water. The formed precipitate was separated, removed, washed thoroughly with pure water and dried at 200° C. for 5 hours.

(II) 190 g of titanium tetrachloride were added gradually to 2000 ml of water. This aqueous solution was heated to 80° C. after which ammonia water was added to the stirred solution to neutralize it. The thus formed precipitate was separated, removed, washed thoroughly with pure water and dried at 200° C. for 5 hours to obtain titanium oxide.

(I), (II) and 100 g of water were mixed, blended well while heating and molded into pellets of 5 mm × 5 mm $\phi$, which were then dried and calcined at 400° C. for 4 hours. The composition of the catalyst expressed by the empirical formula is $Ti_1Cu_{0.2}O_{2.2}$.

Catalyst 2

18.2 g of vanadium pentoxide, the dried titanium oxide prepared from 19 g of titanium tetrachloride in the same manner as in Catalyst 1 (II), 150 g of water and 100 g of α-alumina powder as a carrier were mixed and blended well while heating, after which the blend was molded into pellets of 5 mm × 5 mm $\phi$, dried and calcined at 500° C. for 2 hours. The composition of the catalyst expressed by the empirical formula is $Ti_1V_2O_7\text{-}(\alpha\text{-}Al_2O_3)_{10}$.

Catalyst 3

The dried titanium oxide prepared from 190 g of titanium tetrachloride in the same manner as in Catalyst 1 (II), 80 g of chromium nitrate $Cr(NO_3)_3.9H_2O$ and 150 ml of water were well blended, molded into pellets of 5 mm × 5 mm $\phi$ and dried before calcining at 500° C. for 2 hours. The composition of the catalyst expressed by the empirical formula is $Ti_1Cr_{0.2}O_{2.3}$.

Catalyst 4 to 13

According to the procedures in Catalyst 3, Catalysts 4 to 13 were prepared. The compositions and calcining conditions of the catalysts are shown in Table 1. As the starting materials for the respective components, the following compounds were employed: silver nitrate for Ag, zinc nitrate for Zn, ammonium tungstate for W, ammonium molybdate for Mo, zirconium nitrate for Zr, copper nitrate for Cu, stannic oxide for Sn, gold oxide for Au, magnesium nitrate for Mg, iron nitrate for Fe, lead nitrate for Pb, cobalt nitrate for Co, bismuth nitrate for Bi, nickel nitrate for Ni and manganese nitrate for Mn.

Catalyst 14

19 g of titanium tetrachloride were added gradually to 2000 ml of water. Then 208.3 g of ethyl silicate Si(OEt)$_4$ was added to the aqueous solution and the temperature of the solution was raised to 80° C., after which ammonia water was added thereto to neutralize it. The formed precipitate was separated, removed, washed thoroughly with pure water, and dried at 150° C. for 10 hours to prepare the dried Ti and Si containing product.

22.6 g of stannous chloride $SnCl_2.2H_2O$ were dissolved in 200 ml of water, to which was added ammonia water to neutralize it. 68.1 g of above dried Ti an Si containing product was added to the formed slurry, blended thoroughly while moderately heating, molded into pellets of 5 mm × 5 mm $\phi$ and calcined at 400° C. for 4 hours. The composition of the catalyst expressed by the empirical formula is $Ti_1Si_{10}Sn_1O_{23}$.

Catalyst 15

Using 190 g of titanium tetrachloride and 208.3 g of ethyl silicate and in the same manner as in catalyst 14, the dried Ti and Si containing product was prepared. 26.1 g of ammonium tungstate $5(NH_4)_2O.12WO_3.5H_2O$ and a small amount of water were added to 140 g of this dried product, blended thoroughly, molded into pellets of 5 mm × 5 mm $\phi$, which were then dried and calcined at 400° C. for 4 hours. The composition of the catalyst expressed by the empirical formula is $Ti_1Si_1W_{0.1}O_{4.3}$.

Catalyst 16

In the same manner as in Catalyst 1 (II), the precipitated titanium oxide prepared from 190 g of titanium tetrachloride, 150 g of silica sol (containing 20 wt% as $SiO_2$) and 36.4 g of vanadium pentoxide were well blended, molded into pellets of 5 mm × 5 mm $\phi$ and dried before calcining at 400° C. for 4 hours. The composition of the catalyst expressed by the empirical formula is $Ti_1Si_{0.5}V_{0.4}O_{3.6}$.

Catalyst 17

In the same manner as in Catalyst 14, a catalyst having the empirical formula $Ti_1Si_1Zn_{0.1}Cr_{0.2}O_{4.4}$, except that instead of stannous chloride, chromium nitrate and zinc nitrate were employed.

Catalyst 18

(I) Using 190 g of titanium tetrachloride and 20.8 g of ethyl silicate and in the same manner as in Catalyst 14, the dried Ti and Si containing product was prepared.

(II) 25 g of copper sulfate $CuSO_4.5H_2O$ was dissolved in 250 ml of water and the temperature of the aqueous solution was raised to 70° C. To this solution was added a solution of 15 g of sodium hydroxide in 150 ml of water. The formed precipitate was separated, removed, washed thoroughly with pure water and dried at 200° C. for 5 hours.

(I), (II) and 100 g of water were mixed, blended well while heating and molded into pellets of 5 mm × 5 mm $\phi$, which were then dried and calcined at 400° C. for 4 hours. The composition of the catalyst expressed by the empirical formula is $Ti_1Si_{0.1}Cu_{0.1}O_{2.3}$.

Catalysts 19 to 22

According to the procedures in Catalyst 15, Catalysts 19 to 22 were prepared except that instead of ammonium tungstate, bismuth nitrate, ammonium molybdate, lead nitrate and zirconium nitrate were employed. The compositions and calcining conditions of the catalysts are shown in Table 1.

Catalysts 1 to 22 thus prepared were tested for activity according to the testing method described above. The results are given in Table 1.

Catalyst 23

Water was added to silica alumina powder ($Al_2O_3$ content 26% by weight), blended well and molded into pellets of 5 mm × 5 mm $\phi$. After drying, they were calcined at 500° C. for 2 hours to obtain SiO$_2$.Al$_2$O$_3$ catalyst.

Catalyst 24

Water was added to commercially available titanium oxide powder, blended well and molded into pellets of 5 mm×5 mm $\phi$. After drying, they were calcined at 600° C. for 2 hours to obtain TiO$_2$ catalyst.

Catalysts 25 and 26

190 g of titanium tetrachloride were added gradually to 2000 ml of water. Then, the aqueous solution was heated to a temperature of 80° C., and ammonia water was added thereto to neutralize it. The formed precipitate was separated, removed, washed thoroughly with pure water and dried at 200° C. for 5 hours. Then, water was added to the dried product, blended well and molded into pellets of 5 mm×5 mm $\phi$, which were then calcined at 150° C. and 800° C. respectively to obtain TiO$_2$ catalysts, respectively.

Catalyst 27

18.2 g of vanadium pentoxide were mixed with 100 g of silica alumina powder (alumina content 26% by weight) were mixed well, a small amount of water was added thereto, blended well and molded into pellets of 5 mm×5 mm $\phi$, which were then dried and calcined at 500° C. for 2 hours to obtain V$_2$O$_5$-(SiO$_2$.Al$_2$O$_3$) catalyst.

Catalysts 28 to 31

According to the procedures in Catalyst 27, there were prepared Catalysts 28 to 31 supported on silica alumina. The compositions and calcining conditions of these catalysts are shown in Table 2. As the starting materials, there were employed ammonium tungstate for W, cobalt nitrate for Co, vanadium pentoxide for V and nickel nitrate for Ni.

Catalyst 32

80 g of chromium nitrate Cr(NO$_3$)$_3$.9H$_2$O was dissolved in 200 g of water, to which was added 100 g of α-alumina powder and the mixture was blended well. This was dried at 110° C. for 8 hours and calcined at 500° C. for 2 hours. Then, this was blended with water and molded into pellets of 5 mm×5 mm $\phi$, which were then dried to obtain Cr$_2$O$_3$-(α-Al$_2$O$_3$) catalyst.

Catalyst 33

79.9 g of commercially available titanium oxide, 176.6 g of ammonium molybdate (NH$_4$)$_6$Mo$_7$O$_{27}$.4H$_2$O and 300 ml of water were blended well, molded into pellets of 5 mm×5 mm $\phi$, dried and calcined at 600° C. for 2 hours to obtain a catalyst. The composition of the catalyst expressed by the empirical formula is Ti$_1$Mo$_1$O$_5$.

Catalyst 34

79.9 g of commercially available titanium oxide powder, 202 g of iron nitrate Fe(NO$_3$)$_3$.6H$_2$O and 300 ml of water were blended well, molded into pellets of 5 mm×5 mm $\phi$, dried and calcined at 500° C. for 2 hours to obtain a catalyst. The composition of the catalyst expressed by the empirical formula is Ti$_1$Fe$_{0.5}$O$_{2.8}$.

Catalyst 35

(I) 125.0 g of copper sulfate CuSO$_4$.5H$_2$O were dissolved in 500 ml of water and the temperature of the aqueous solution was raised to 70° C. To the solution was added a solution of 80 g of sodium hydroxide in water (300 ml). The formed precipitate was separated, removed, washed with pure water thoroughly and dried at 200° C. for 5 hours.

(II) Titanium oxide was prepared from 19.0 g of titanium tetrachloride in the same manner as in Catalyst 26.

(I), (II) and 100 g of water were mixed and blended well while moderately heating, molded into pellets of 5 mm×5 mm $\phi$, dried and calcined at 800° C. for 4 hours. The composition of the catalyst expressed as the empirical formula is Ti$_1$Cu$_5$O$_7$.

Catalysts 23 to 35 thus prepared were tested for activity according to the testing method described above. The results are shown in Table 2.

TABLE 1

| | | (Present Invention) | | | | | | | | |
|---|---|---|---|---|---|---|---|---|---|---|
| | | Calcining Conditions | | | | Reaction Conditions | | Results of Reaction | | |
| Cat. No. | Composition (Atomic ratio) | Temp. (°C.) | Time (hr) | Reactants | | | Temp. (°C.) | S.V. (hr$^{-1}$) | Product | Conv. (%) | Selec. (%) |
| | | | | Nitrile | Alcohol | Water | | | | | |
| 1 | Ti$_1$Cu$_{0.2}$O$_{2.2}$ | 400 | 4 | MAN | MeOH | Water | 230 | 100 | MMA | 68.9 | 77.8 |
| | | | | PNT | EtOH | Water | 230 | 100 | EPA | 63.5 | 78.1 |
| 2 | Ti$_1$V$_2$O$_7$-(α-Al$_2$O$_3$) | 500 | 2 | MAN | MeOH | Water | 250 | 50 | MMA | 45.9 | 72.3 |
| 3 | Ti$_1$Cr$_{0.2}$O$_{2.3}$ | 500 | 2 | MAN | MeOH | Water | 250 | 100 | MMA | 62.1 | 74.6 |
| 4 | Ti$_1$Ag$_{0.2}$O$_{2.1}$ | 500 | 2 | MAN | MeOH | Water | 230 | 100 | MMA | 65.2 | 79.1 |
| 5 | Ti$_1$Zn$_{0.05}$O$_{2.1}$ | 400 | 4 | MAN | MeOH | Water | 250 | 100 | MMA | 61.6 | 74.9 |
| 6 | Ti$_1$W$_{0.1}$O$_{2.3}$ | 600 | 2 | MAN | MeOH | Water | 230 | 200 | MMA | 60.8 | 84.0 |
| | | | | BNT | MeOH | Water | 270 | 100 | MBA | 38.6 | 57.7 |
| 7 | Ti$_1$Mo$_{0.05}$O$_{2.2}$ | 600 | 2 | MAN | MeOH | Water | 230 | 200 | MMA | 69.2 | 71.7 |
| 8 | Ti$_1$Zr$_1$Cu$_{0.5}$O$_{4.5}$ | 600 | 2 | AN | EtOH | Water | 230 | 100 | EAA | 72.9 | 51.3 |
| | | | | MAN | MeOH | Water | 230 | 100 | MMA | 68.4 | 74.9 |
| 9 | Ti$_1$Sn$_5$O$_{12}$ | 400 | 4 | MAN | MeOH | Water | 210 | 100 | MMA | 55.2 | 73.9 |
| 10 | Ti$_1$Au$_{0.2}$O$_{2.1}$ | 500 | 2 | MAN | MeOH | Water | 230 | 100 | MMA | 63.3 | 78.2 |
| 11 | Ti$_1$Mg$_{0.05}$Fe$_{0.1}$O$_{2.2}$ | 500 | 2 | MAN | MeOH | Water | 230 | 100 | MMA | 62.4 | 70.8 |
| 12 | Ti$_1$Pb$_{0.05}$Co$_{0.1}$O$_{2.2}$ | 400 | 4 | AN | MeOH | Water | 230 | 200 | MAA | 64.1 | 62.7 |
| 13 | Ti$_1$Bi$_{0.06}$Ni$_{0.2}$Mn$_{0.1}$O$_{2.4}$ | 400 | 4 | AN | MeOH | Water | 250 | 500 | MAA | 50.1 | 72.4 |
| 14 | Ti$_1$Si$_{10}$Sn$_1$O$_{23}$ | 400 | 4 | MAN | MeOH | Water | 230 | 100 | MMA | 77.3 | 80.1 |
| 15 | Ti$_1$Si$_1$W$_{0.1}$O$_{4.3}$ | 400 | 4 | MAN | MeOH | Water | 230 | 200 | MMA | 61.7 | 87.3 |
| 16 | Ti$_1$Si$_{0.5}$V$_{0.4}$O$_{3.6}$ | 400 | 4 | MAN | MeOH | Water | 200 | 100 | MMA | 68.8 | 83.4 |
| 17 | Ti$_1$Si$_1$Zn$_{0.1}$Cr$_{0.2}$O$_{4.4}$ | 400 | 4 | PNT | EtOH | Water | 230 | 100 | EPA | 70.3 | 78.8 |
| 18 | Ti$_1$Si$_{0.1}$Cu$_{0.1}$O$_{2.3}$ | 400 | 4 | MAN | MeOH | Water | 210 | 100 | MMA | 82.0 | 73.5 |
| 19 | Ti$_1$Si$_2$Bi$_{0.2}$O$_{6.3}$ | 400 | 4 | MAN | MeOH | Water | 210 | 100 | MMA | 66.5 | 79.1 |
| 20 | Ti$_1$Si$_1$Mo$_{0.2}$O$_{4.8}$ | 400 | 4 | MAN | MeOH | Water | 210 | 100 | MMA | 78.2 | 64.8 |
| 21 | Ti$_1$Si$_{0.1}$Pb$_{0.05}$O$_{2.25}$ | 400 | 4 | MAN | MeOH | Water | 230 | 100 | MMA | 68.4 | 73.3 |

TABLE 1-continued (Present Invention)

| Cat. No. | Composition (Atomic ratio) | Calcining Conditions Temp. (°C.) | Calcining Conditions Time (hr) | Reactants Nitrile | Reactants Alcohol | Reactants Water | Reaction Conditions Temp. (°C.) | Reaction Conditions S.V. (hr$^{-1}$) | Results of Reaction Product | Results of Reaction Conv. (%) | Results of Reaction Selec. (%) |
|---|---|---|---|---|---|---|---|---|---|---|---|
| 22 | Ti$_1$Si$_1$Zr$_2$O$_8$ | 400 | 4 | MAN | MeOH | Water | 210 | 100 | MMA | 66.4 | 74.6 |

TABLE 2

(Comparative)

| Cat. No. | Composition (Atomic ratio) | Calcining Conditions Temp. (°C.) | Calcining Conditions Time (hr) | Reactants Nitrile | Reactants Alcohol | Reactants Water | Reaction Conditions Temp. (°C.) | Reaction Conditions S.V. (hr$^{-1}$) | Results of Reaction Product | Results of Reaction Conv. (%) | Results of Reaction Selec. (%) |
|---|---|---|---|---|---|---|---|---|---|---|---|
| 23 | SiO$_2$.Al$_2$O$_3$ | 500 | 2 | MAN | MeOH | Water | 230 | 100 | MMA | 7.5 | 62.3 |
| 24 | TiO$_2$ (commercial) | 600 | 2 | MAN | MeOH | Water | 230 | 100 | MMA | 15.0 | 40.2 |
| 25 | TiO$_2$ | 150 | 2 | MAN | MeOH | Water | 210 | 100 | MMA | 60.4 | 39.3 |
| 26 | TiO$_2$ | 800 | 2 | MAN | MeOH | Water | 250 | 100 | MMA | 47.5 | 53.3 |
| 27 | V$_2$O$_5$.SiO$_2$.Al$_2$O$_3$ | 500 | 2 | MAN | MeOH | Water | 230 | 100 | MMA | 8.5 | 91.5 |
| 28 | WO$_3$.SiO$_2$.Al$_2$O$_3$ | 500 | 2 | MAN | MeOH | Water | 230 | 100 | MMA | 8.8 | 91.0 |
| 29 | CoO.SiO$_2$.Al$_2$O$_3$ | 500 | 2 | MAN | MeOH | Water | 230 | 100 | MMA | 9.0 | 63.9 |
| 30 | Co$_1$V$_1$O$_{3.5}$.SiO$_2$.Al$_2$O$_3$ | 500 | 2 | MAN | MeOH | Water | 230 | 100 | MMA | 9.3 | 80.6 |
| 31 | NiO.SiO$_2$.Al$_2$O$_3$ | 500 | 2 | MAN | MeOH | Water | 230 | 100 | MMA | 7.2 | 41.5 |
| 32 | Cr$_2$O$_3$.α-Al$_2$O$_3$ | 500 | 2 | MAN | MeOH | Water | 230 | 100 | MMA | 7.6 | 60.8 |
| 33 | Ti$_1$Mo$_1$O$_5$ | 600 | 2 | MAN | MeOH | Water | 230 | 100 | MMA | 18.6 | 47.8 |
| 34 | Ti$_1$Fe$_{0.5}$O$_{2.8}$ | 500 | 2 | MAN | MeOH | Water | 230 | 100 | MMA | 21.2 | 57.4 |
| 35 | Ti$_1$Cu$_5$O$_7$ | 800 | 2 | MAN | MeOH | Water | 230 | 100 | MMA | 27.3 | 62.1 |

Abbreviatons in the Tables

AN: Acrylonitrile
BNT: Benzonitrile
Conv.: Percent Conversion
EAA: Ethyl Acrylate
EPA: Ethyl Propionate
EtOH: Ethyl Alcohol
MBA: Methyl Benzoate
MeOH: Methyl Alcohol
MAA: Methyl Acrylate
MMA: Methyl Methacrylate
MAN: Methacrylonitrile
PNT: Propionitrile
Selec.: Percent Selectivity As is apparent from the above Tables 1 and 2, the titanium containing oxide catalyst mixed with at least one specific element prepared in accordance with the process of this invention exhibits superior properties such as a high percent conversion of nitriles and a high selectivity for the ester.

While the invention has been described in detail and with reference to specific embodiments thereof, it will be apparent to one skilled in the art that various changes and modifications can be made therein without departing from the spirit and scope thereof.

What is claimed is:

1. In a process for preparing a carboxylic acid ester from a nitrile, water and alcohol in the vapor phase, wherein the vapor is brought into contact with a catalyst, the improvement which comprises said catalyst being a titanium containing oxide catalyst which is obtained by hydrolyzing or neutralizing a water soluble titanium salt and subsequently calcining the resulting precipitate at a temperature in a range of about 300° to 750° C. and having the empirical formula Ti$_a$Me$_b$X$_c$O$_d$, wherein Me represents at least one element selected from the group consisting of Cu, Ag, Au, Mg, Zn, Sn, Pb, Zr, V, Bi, Cr, W, Mo, Mn, Fe, Co, and Ni and X represents at least one element selected from the group consisting of Si and Sb and the subscripts a, b, c and d designate the atomic ratio and when a is 1, b is 0.01 to 12, c is 0 to 12 and b+c is 0.01 to 12 and d is the oxygen content of the catalyst formed by the combination of the above components.

2. The process according to claim 1, wherein said titanium containing oxide catalyst has the empirical formula Ti$_a$Me$_b$X$_c$O$_d$, wherein Me represents at least one element selected from the group consisting of Cu, Ag, Au, Sn, Pb, Zr, V, Bi, Mo and W and X represents Si and the subscripts a, b, c and d designate the atomic ratio and when a is 1, b is 0.01 to 12, c is 0 to 12 and b+c is 0.01 to 12 and d is the oxygen content of the catalyst formed by the combination of the above components.

3. The process according to claim 1 in which the water soluble titanium salt is selected from the group consisting of titanium chloride, nitrate, sulfate and their mixtures.

4. The process according to claim 1 in which the neutralization or hydrolysis of the water soluble titanium salt is carried out at a temperature of about 0° to 100° C.

5. The process according to claim 1 in which the nitrile is selected from the group consisting of acetonitrile, propionitrile, acrylonitrile, methacrylonitrile, benzonitrile and their mixtures.

6. The process according to claim 1 in which the alcohol is selected from the group consisting of methyl alcohol, ethyl alcohol, n-propyl alcohol, isopropyl alcohol, butyl alcohol and their mixtures.

7. The process according to claim 1, wherein said carboxylic acid ester is an ester of an α,β unsaturated acid.

8. The process according to claim 1, wherein said carboxylic acid ester is an acrylic acid ester.

9. The process according to claim 1, wherein said carboxylic acid ester is methylmethacrylate.

10. The process according to claim 1, 3, 4, 5, 6, 7, 8, or 9, wherein X is Si.

* * * * *